United States Patent [19]
Lee et al.

[11] Patent Number: 5,459,574
[45] Date of Patent: Oct. 17, 1995

[54] OFF-LINE-LOCKED LASER DIODE SPECIES MONITOR SYSTEM

[75] Inventors: Jamine Lee, Burlington; Neil Goldstein, Belmont; Steven Richtsmeier, Tewksbury; Fritz Bien, Concord; Michael Gersh, Bedford, all of Mass.

[73] Assignee: Spectral Sciences Inc., Burlington, Mass.

[21] Appl. No.: 324,101

[22] Filed: Oct. 14, 1994

[51] Int. Cl.$^6$ ................................................. G01N 21/61
[52] U.S. Cl. ................................................................ 356/437
[58] Field of Search ....................................... 356/437, 438, 356/439, 409; 250/343

[56] References Cited

U.S. PATENT DOCUMENTS

5,026,991   6/1991   Goldstein et al. .................... 250/343
5,047,639   9/1991   Wong ................................... 356/436
5,202,560   4/1993   Koch et al. .......................... 356/435

Primary Examiner—Richard A. Rosenberger
Attorney, Agent, or Firm—Iandiorio & Teska

[57] ABSTRACT

An off-line-locked laser diode species monitor system includes: reference means for including at least one known species having a first absorption wavelength; a laser source for irradiating the reference means and at least one sample species having a second absorption wavelength differing from the first absorption wavelength by a predetermined amount; means for locking the wavelength of the laser source to the first wavelength of the at least one known species in the reference means; a controller for defeating the means for locking and for displacing the laser source wavelength from said first absorption wavelength by said predetermined amount to the second absorption wavelength; and a sample detector device for determining laser radiation absorption at the second wavelength transmitted through the sample to detect the presence of the at least one sample species.

44 Claims, 3 Drawing Sheets

OFF-LINE-LOCKED LASER DIODE SPECIES MONITOR SYSTEM

GOVERNMENT RIGHTS

This invention was made with government support a under Contract No. NAS8-40162 with NASA and Contract No. DE-FG02-94ER81865 with the DOE. The government has certain rights in this invention.

FIELD OF INVENTION

This invention relates to an off-line-locked laser diode species monitor system.

BACKGROUND OF INVENTION

The detection of concentrations of various gaseous species in ambient air and in other environments with varying temperature and/or pressure conditions has become ever more important. Potential applications include industrial process streams such as dryers, process columns, or combustors, as well as monitoring of toxic species in ambient environments. Diode laser systems have been used to measure these various gaseous species. In these systems a laser beam is directed through a sample region containing a gas or gases, each of which absorb laser energy at particular wavelengths. The type of gas or gases in the region can be determined by noting the wavelength(s) of the energy absorbed or more typically by supplying the region with a known wavelength which corresponds to the absorption wavelength of a particular gaseous species of interest. The concentration of the gas can be computed from the pressure, temperature, and the amount of absorption, which may be accomplished by comparing the amount of incident radiation to the amount of transmitted radiation: the greater the absorption, the greater the species concentration.

Maintaining a lock on and continuously outputting a laser wavelength equal to the absorption wavelength of a particular species being monitored is crucial to obtaining accurate concentration measurements. However, this is difficult due to laser wavelength drifts away from coincidence with the species absorption wavelength. To ensure accurate real-time concentration monitoring under changing conditions a wavelength-locked laser gaseous species monitor system, as disclosed in U.S. Pat. No. 5,026,991 (the '991 patent), was developed. That patent is incorporated herein by reference in its entirety. The system disclosed in that patent utilizes a reference cell containing a known concentration of the gaseous species to be monitored in a feedback loop so that the laser wavelength (corresponding to the species absorption wavelength) can be continuously monitored and adjusted over time in order to lock it to the absorption line wavelength of the species being monitored.

Certain species, however, cannot be contained in a reference cell because such species react with or corrode the reference cell. For example, HF will corrode the optics of the cell. Also, unstable or transient species, such as OH and CH, are not viable under ambient reference cell conditions. These species exist only under certain pressure and temperature conditions. Finally, internally excited states of stable species may have very low concentrations at ambient reference cell conditions. Nevertheless, it is still desirable to measure the concentrations of these types of species accurately.

One method that does not require a reference cell but is capable of measuring the concentration(s) of species not capable of being contained in a reference cell is Fourier Transform Infrared (FTIR) spectroscopy. However, this method is not suitable for making measurements in environments where species concentration are varying rapidly over time. Moreover, systems for performing FTIR spectroscopy are large, expensive and slow.

Another method not requiring the containment of a sample in a reference cell of the gaseous species to be measured is laser diode spectroscopy. With this method the laser is scanned over the entire spectrum and is not locked to a single absorption line. Because of this the system is slow, requiring scanning of the entire spectrum even though only a single wavelength may be of interest. Moreover, this method is not very sensitive and it makes monitoring concentration variations very difficult as the species is not being continuously monitored.

Spectroscopy with a broad band radiation source does enable monitoring of species without a reference cell. However, since the band pass is not narrow it is susceptible to interfering species, and it is less sensitive.

SUMMARY OF INVENTION

It is therefore an object of this invention to provide an off-line-locked laser diode species monitor system.

It is a further object of this invention to provide such an off-line-locked laser diode species monitor system which enables accurate monitoring of species without requiring the containment of a sample of the species being monitored in a reference cell.

It is a further object of this invention to provide such an off-line-locked laser diode species monitor system which enables high sensitivity species concentration monitoring typically associated with line-locking feedback monitor systems without requiring line-locking to the wavelength of the species being monitored.

It is a further object of this invention to provide such an off-line-locked laser diode species monitor system which is capable of accurately monitoring transient, unstable and corrosive species.

It is a further object of this invention to provide such an off-line-locked laser diode species monitor system that has a short response time and is capable of real-time monitoring.

It is a further object of this invention to provide such an off-line-locked laser diode species monitor system which enables accurate species monitoring under varying temperature and pressure conditions.

It is a further object of this invention to provide such an off-line-locked laser diode species monitor system that does not scan the laser across a broad wavelength band.

It is a further object of this invention to provide such an off-line-locked laser diode species monitor system that is relatively simple and inexpensive.

It is a further object of this invention to provide such an off-line-locked laser diode species monitor system with good temporal resolution.

It is a further object of this invention to provide such an off-line-locked laser diode species monitor system with long-term stability.

It is a further object of this invention to provide such an off-line-locked laser diode species monitor system which is compact.

This invention results from the realization that a truly effective off-line-locked laser diode species monitor system can be achieved by providing a reference means which includes one known species having a first absorption wavelength and a laser source that irradiates the reference means and a sample species which has a second absorption wavelength which differs from the first wavelength by a predetermined amount, and from the further realization that the laser source may be locked to the one known species in the reference means and periodically displaced by a predetermined wavelength difference to a second absorption wavelength to detect laser radiation absorption at the second wavelength transmitted through the sample to detect the presence of the at least one sample species.

This invention features an off-line-locked laser diode species monitor system. The system includes reference means for including at least one known species having a first absorption wavelength. There is also included a laser source for irradiating the reference means and at least one sample species to be monitored having a second absorption wavelength differing from said first absorption wavelength by a predetermined amount. There are means for locking the wavelength of the laser source to the first wavelength of the at least one known species in the reference means and there is a controller for defeating the means for locking and for displacing the laser source wavelength from the first absorption wavelength by the predetermined amount to the second absorption wavelength. Finally, there is a sample detector device for determining laser radiation absorption at the second wavelength transmitted by the sample to detect the presence of the at least one sample species.

In a preferred embodiment the reference means may include a reference cell device or it may be a measurement region. The laser source may include a laser diode. The laser source may include a laser wavelength controller for adjusting the current supplied to and the temperature of the diode laser to vary the wavelength of the output. The sample species may be a gas which corrosively reacts with the reference cell or it may be a transient or unstable species. The sample species may be an excited internal state of a stable species with a low concentration under ambient conditions. The sample species and the known species may be contained in a measurement region. The means for locking may include a reference sensor device, responsive to the reference means, for producing an error signal proportional to the difference between the diode laser wavelength and the absorption wavelength of the known species. The reference sensor device may be a phase sensitive detector and the error signal may be an odd harmonic component of the radiation transmitted through the reference species. The means for locking may further include a locking circuit, responsive to the reference sensor device, for receiving the error signal and for generating from the error signal a correction signal. There may further be included a control circuit, responsive to the locking circuit and the controller, for combining the error signal and a first set signal from the controller to provide a first drive signal to drive the laser source at the first absorption wavelength. The controller may include means for selectively defeating the error signal delivered to the locking circuit and for supplying a second set signal to the control circuit to be combined with the correction signal to provide a second drive signal to drive the laser diode from the first absorption wavelength to the second absorption wavelength of the sample species. The controller may further include means for periodically actuating the control circuit to defeat the error signal delivered to the locking circuit and to supply the second set signal. The controller may further include means for supplying a temperature signal to the control circuit to maintain the laser source at a desired temperature. The sample detector device may include means for determining laser radiation absorption at the first wavelength of the at least one known species when the laser source is locked to the first wavelength for detecting the presence of the at least one known species in the measurement region. There may further be included means, responsive to the means for determining, for resolving the concentration of the at least one known species. There may further be included means, responsive to the means for determining, for resolving the concentration of the at least one sample species. The controller may include means for driving the laser source at a plurality of second absorption wavelengths corresponding to a plurality of sample species and the sample detector may include means for determining laser radiation absorption at the plurality of second absorption wavelengths transmitted through the sample species to detect the presence of the plurality of sample species. The means for locking may include means for locking to a plurality of known species in the reference means. The controller may include means for driving the laser source at a plurality of second absorption wavelengths corresponding to a plurality of absorption features of the at least one sample species and the sample detector means may include means for determining laser radiation absorption at the plurality of second absorption wavelengths transmitted through the sample species to obtain absorption feature information.

This invention also features an off-line-locked laser diode species monitor system with a reference cell device for including at least one known species having a first absorption wavelength. There is included a diode laser for irradiating the reference cell device and at least one sample species to be monitored having a second absorption wavelength differing from the first absorption wavelength by a predetermined amount. There is also a reference sensor device, responsive to the reference cell device, for detecting the diode laser radiation transmitted by the reference cell device and a control circuit, responsive to the reference sensor device, for providing a first drive signal to the laser diode to lock the diode laser output wavelength to the first absorption wavelength of the species in the reference cell device. There is also included a controller for selectively actuating the control circuit to defeat the laser diode lock and to generate a second drive signal to drive the laser diode from the first absorption wavelength to the second absorption wavelength of the sample species to be monitored. There is also included a sample detector device for determining the laser radiation absorption at the second wavelength transmitted through the sample to detect the presence of the at least one sample species.

In a preferred embodiment the diode laser may include a laser wavelength controller for adjusting the diode laser input current and temperature for varying the diode laser output wavelength. The sample species may corrode the reference cell or the sample species may be a transient or unstable species. The sample species may be an excited internal state of a stable species with a low concentration under ambient conditions. The sample species and the known species may be contained in a measurement region. The reference sensor device may produce an error signal proportional to the difference between the diode laser wavelength and the absorption wavelength of the known species. The reference sensor device may be a phase sensitive detector and the error signal may be an odd harmonic component of the diode laser radiation transmitted through the reference species. The control circuit may include a locking circuit, responsive to the reference sensor device, for receiving the error signal from the reference sensor device and for generating from the error signal a correction signal. The control circuit may further include means for combining the correction signal and a first set signal received from the controller to generate the first drive signal to drive the laser diode output at the first absorption wavelength. The controller may further include means for selectively defeating the error signal delivered to the locking circuit and for supplying a second set signal to the means for combining to combine the second set signal and the correction signal to generate the second drive signal to drive the laser diode output at the second absorption wavelength. The sample detector device may include means for determining laser radiation absorption at the first wavelength of the at least one known species when the laser diode has an output wavelength equal to the first absorption wavelength to detect the presence of the at least one known species in the measurement region. There may also be included means, responsive to the sample detector device, for resolving the concentration of the known species detected. There may further be included means, responsive to the sample detective device, for resolving the concentration of the at least one sample species detected. The controller may include means for supplying a temperature signal to the control circuit to maintain the laser source at a desired temperature. The controller may also include means for driving the laser source at a plurality of second absorption wavelengths corresponding to a plurality of sample species and the sample detector may include means for determining laser radiation absorption at the plurality of second absorption wavelengths transmitted through the sample species to detect the presence of the plurality of sample species. The control circuit may include means for locking to a plurality of known species in the reference cell device. The controller may include means for driving the laser source at a plurality of second absorption wavelengths corresponding to a plurality of absorption features of the at least one sample species and the sample detector means may include means for determining laser radiation absorption at the plurality of second absorption wavelengths transmitted through the sample species to obtain absorption feature information.

DISCLOSURE OF PREFERRED EMBODIMENT

Other objects, features and advantages will occur to those skilled in the art from the following description of a preferred embodiment and the accompanying drawings, in which.

Figure 1:
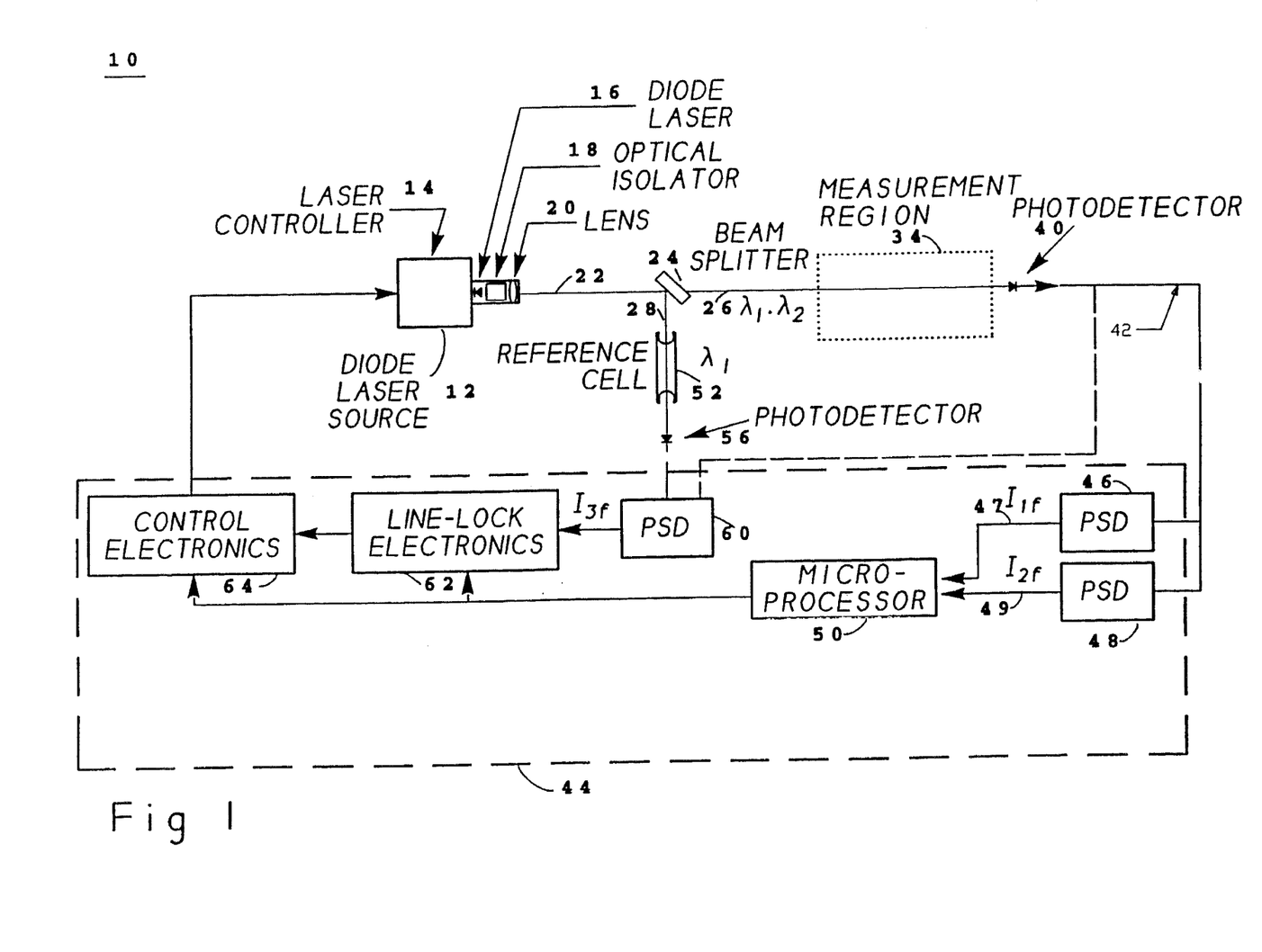
FIG. 1 is a schematic block diagram of the off-line-locked laser diode species monitor system according to this invention.

In FIG. 1 there is shown off-line-locked laser diode monitor system 10 for detecting the presence of and/or concentration of one or more gaseous species. The system includes laser source 12 which is comprised of laser controller 14 which controls the laser drive current and operating temperature of diode laser 16. Laser source 12 also includes optical isolator 18 and lens 20. A laser beam 22 from laser source 12 is initially at the absorption wavelength, $\lambda_1$, of a known reference species. Laser source 12 is initially line-locked to this species absorption wavelength by known techniques which are described in more detail below and are fully described in the '991 patent.

Laser beam 22 impinges on beam splitter 24 which directs the beam along two paths 26 and 28. The majority of the beam is directed along path 26 and introduced to measurement region 34. Measurement region 34 may be any region including the inside of a probe or sensor head or it may be an open region. The beam is then received by photodetector 40 which converts the beam to an electrical signal and delivers that electrical signal over line 42 to control and measurement electronics 44. Within control and measurement electronics 44 the signal from line 42 is introduced to phase sensitive detectors 46 and 48. Phase sensitive detector 46 outputs over line 47 the first harmonic component of the signal or, alternatively in the absence of a phase sensitive detector, the DC signal, which is used to determine the laser beam intensity in measurement region 34. Phase sensitive detector 48 outputs over line 49 an even harmonic component of the signal. In this example it is the second harmonic; however, it could be any even harmonic greater than or equal to the second harmonic. The second harmonic signal is used to measure the absorption of the known species within the measurement region 34 as is known and fully described in the '991 patent. Both the first and second harmonic signal components are input to microprocessor 50 which performs a normalizing function by dividing the second harmonic signal by the first harmonic (or the DC) signal to determine absolute absorption. This normalizing function is performed to account for variations in intensity of laser beam 26 and/or unclean optics. This value is stored in the memory of microprocessor 50 and identified with a particular measurement time, indicating the presence of the species being monitored (the reference species in this case) for that given time. In addition, the absolute absorption value may be used in conjunction with pressure and temperature readings from the measurement region to calculate concentration of the species at a given time. This process is known and is more fully described in the '991 patent.

In order to obtain accurate absorption measurements at a particular wavelength, in this case at the absorption wavelength, $\lambda_1$, of the known reference species, maintaining a line-lock on that wavelength is crucial. The method for obtaining such a line-lock is fully described in the '991 patent; however, it is also briefly described below as follows.

If there is insufficient absorption by the reference species in measurement region 34 after laser beam 22 passes through beamsplitter 24 a small portion of the beam is directed along path 28 and passes through reference cell 52 which contains a known quantity of the reference species which has an absorption wavelength $\lambda_1$. After the beam exits the reference cell 52 it falls on a photodetector 56 which converts the light energy to an electrical signal and applies the electrical signal to phase sensitive detector 60. If there is sufficient absorption in measurement region 34, the signal from photodetector may be fed directly to phase sensitive detector 60. Laser controller 12 initially drives diode laser 16 with a drive current and at a temperature such that the output wavelength of the laser diode is at or near the absorption wavelength of the known reference species contained within the reference cell 52. The temperature and current information for the known reference species is contained within the memory of microprocessor 50. Once laser source 12 is operating at or near the absorption wavelength, it is modulated by laser controller 12 about that wavelength. The modulated output, after being passed through reference species and photodetector 56 or 40, is introduced to phase sensitive detector 60 which supplies line-lock electronics 62 with the determined error signal, $S_{error}$, which is the third or higher odd harmonic signal component of the signal introduced to phase sensitive detector 60. Line-lock electronics 62 takes the error signal and outputs a correction signal, $S_{error}$, to control electronics 64. This signal occurs only when the laser output wavelength over lines 22 and 28 is not coincident with the absorption wavelength $\lambda_1$ of the known species in the reference cell. When these wavelengths are coincident, the signal is zero and the diode laser 16 is outputting the laser beam at the proper wavelength for determining absorption of the known species which has an absorption wavelength $\lambda_1$. If it is determined that the error signal is not zero, a correction signal $\pm S_{correct}$ is delivered to control electronics 64 to drive the diode laser to wavelength $\lambda_1$. This process is fully described in the '991 patent.

There are two other inputs to control electronics 64 which originate from microprocessor 50. These inputs include the initial DC set signal, $S_{ini\lambda_1}$, which causes the laser controller 12 to output a laser beam with a wavelength at or near the wavelength of the reference species in the reference cell 52 and the amplitude of the AC modulation signal, $S_{AC}$, which causes the laser wavelength output to be modulated about the output wavelength. Control electronics 64 combines these three signals; namely, the correction signal, $S_{correct}$, from-line electronics 62, the initial set signal, $S_{ini\lambda_1}$, and the AC modulation signal, $S_{AC}$. Microprocessor 50 also supplies control electronics 64 with a signal, $T_{set}$, representative of the operating temperature required for diode laser 16 to output the appropriate laser wavelength. Thus, control electronics 64 supplies laser controller 12 with a temperature signal as well as the combined signal which in conjunction allow laser controller 12 to drive diode laser 16 at a drive current, $i_{drive\lambda_1}$, and temperature $T_{set}$ to achieve the appropriate wavelength, $\lambda_1$, when the line-lock is being maintained.

In order to achieve line-lock and maintain the line-lock, the laser wavelength must initially be set close enough to the absorption line $\lambda_1$ of the reference species within reference cell 52 so that the bandwidth of the modulated signal encompasses at least a part of that absorption line. If the initial laser wavelength is so far from the absorption line that there is no overlap, no feedback signal will be generated by line-lock electronics 62. Thus, it is necessary to choose in advance an absorption line to be monitored and cause to be stored the drive current and temperature necessary to achieve such a line-lock. A system for achieving the line-lock automatically, that is, by simply initiating operation of the system, and which also after unexpected shutdown may be powered up and automatically re-locked, is described in a patent application by the present inventors entitled "System and Method for Achieving Wavelength Lock" filed Sep.22, 1994. That application is incorporated herein in its entirety by reference.

Figure 2:
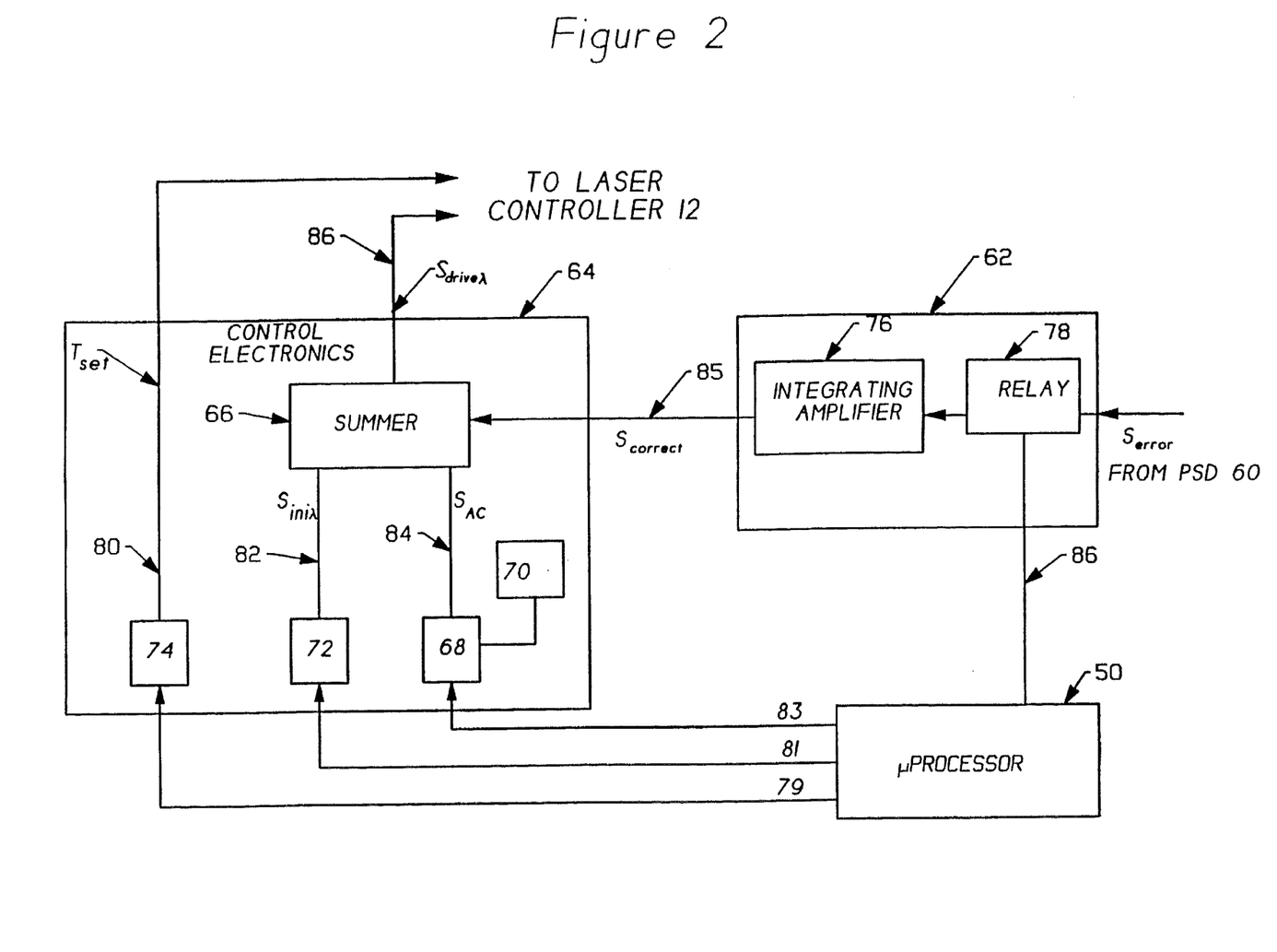
FIG. 2 is a more detailed schematic block diagram of the control electronics and line-lock electronics of FIG. 1.

Control electronics 64 and line-lock electronics 62 are shown in more detail in FIG. 2. Control electronics 64 is shown to include summer 66, AC modulation current amplitude DAC 68, sine wave generator 70, DC set signal DAC 72 and temperature set DAC 74. Line-lock electronics 62 includes integrating amplifier 76 and relay 78.

Microprocessor 50 supplies a digital temperature set signal over line 79 to temperature set DAC 74 which converts the digital signal to an analog signal, $T_{set}$, which is delivered to laser controller 12 over line 80 to operate diode laser 16 at the appropriate temperature. Microprocessor 50 also outputs a digital signal over line 81 corresponding to the DC set signal required to drive diode laser 16 at or near $\lambda_1$ to DC set signal DAC 72. DC set signal DAC 72 supplies a corresponding analog signal, $S_{ini\lambda_1}$, over line 82 to summer 66. Finally, microprocessor 50 supplies a digital signal over line 83 to AC modulation amplitude DAC 68. This signal determines the amplitude of a sinewave signal generated by sinewave generator 70, $S_{AC}$, which is supplied over line 84 to summer 66.

Line-lock electronics 62 receives from phase sensitive detector 60, FIG. 1, the error signal, $S_{error}$, which is introduced through relay 78 to the integrating amplifier 76 which integrates the error signal and delivers a correction signal, $S_{correct}$, over line 85 to summer 66 of control electronics 64. Microprocessor 50 is capable of selectively or periodically providing relay 78 of line-lock electronics 62 with a disable signal over line 86 which will be discussed in more detail below.

In operation, when the diode laser is to be initially locked to the absorption wavelength of the reference species, $\lambda_1$, microprocessor 50 supplies the temperature set signal, DC set signal and AC modulation amplitude signal to control electronics 64 over lines 79, 81, 83, respectively. The temperature set signal microprocessor 50 is converted to an analog signal and is supplied to laser controller 12, FIG. 1, by temperature set DAC 74. The summer 66 sums the DC set signal, $S_{ini\lambda_1}$, frown DC set signal DAC 72, the AC amplitude modulation signal, $S_{AC}$, and the correction signal, $S_{correct}$, to obtain the drive signal, $S_{drive\lambda_1}$, which is delivered over line 86 to laser controller 12, FIG. 1. The output of laser controller 12 is a current, $i_{drive\lambda_1}$, proportional to these three signals, $S_{ini\lambda_1}$, $S_{AC}$ and $S_{correct}$ to drive the diode laser 16 at $\lambda_1$.

The process described above is suitable for detecting and determining the concentration of the reference species in a measurement region. However, as described above, there are certain sample species for which it is desirable to determine their presence and concentration but whose absorption feature to be probed cannot be contained within a reference cell. These sample species include transient, chemically unstable, corrosive species and an excited internal state of a stable species with a low concentration under ambient conditions. Nevertheless, accurate concentration measurements of these features are still desirable. The absorption wavelength, $\lambda_2$, is known for these sample species which cannot be contained within a reference cell. The laser wavelength where a diode laser operates can be characterized by a current for any fixed temperature. Consequently, the laser may be periodically tuned from wavelength $\lambda_1$ to $\lambda_2$ by introducing a known current offset, $\Delta i$. Since the laser current is periodically switched back and forth on a time scale short compared to that for laser wavelength drift, the lock to $\lambda_1$ serves to keep the laser coincident with the absorption of the sample $\lambda_2$. The sample concentration may be determined by averaging the sample concentration measurements over a number of measurement periods.

The duty cycle for this process is described in detail for a typical line-lock electronics system as follows. In order to monitor the absorption of the sample species in the measurement region 34 sometime after line-lock on the reference wavelength $\lambda_1$ has been achieved, microprocessor 50 supplies control electronics 64 with a new DC set signal, $S_{ini\lambda_1}$, which is offset from $S_{ini\lambda_1}$ by $\Delta S$ corresponding to the current which will enable laser controller 12, FIG. 1, to operate diode laser 16 at a wavelength, $\lambda_2$, displaced by $\Delta\lambda$ from $\lambda_1$. At the same time, microprocessor 50 sends a disable signal over line 86 to relay 78 of line-lock electronics 62. This prevents integrating amplifier 76 from responding to the error signal generated at $\lambda_2$. The input over line 85 to summer 66 remains at $S_{correct}$ until the line-lock input signal is reinstituted by enabling relay 78. Thus, there is a new drive current, $i_{drive\lambda_2}$, supplied by laser controller 12 which is proportional to the sum of the new DC set signal, $S_{ini\lambda_2}$, from the microprocessor, the AC modulation signal, $S_{AC}$, and the previous correction signal, $S_{correct}$, from the line-lock electronics 62. The laser controller 12 then causes diode laser 16 to output a laser beam wavelength at $\lambda_2$, the absorption wavelength of the sample species which is to be monitored within measurement region 34. The laser beam at this wavelength is transmitted through measurement region 34, converted to an electrical signal and passed to microprocessor 50 where the detection and concentration of the sample species may be logged. After a short measurement period, microprocessor 50 halts data collection and restores the signal setting to $S_{ini\lambda_1}$ for operation at $\lambda_1$. After the laser and detection electronics have stabilized, the microprocessor 50 enables relay 78 to reinstate the line-lock input signal. Thus, this process allows for very accurate detection and concentration measurement of species that are not containable in a reference cell by disabling the input to the line-lock and offsetting the current by a known amount in order to output a laser wavelength at the wavelength of the sample species. If the line lock is refreshed frequently, approximately once every 50 ms, the sample species can be very accurately monitored without encountering the drift problems generally associated with an unlocked detection system.

Alternate means of refreshing the line lock will be obvious to those skilled in the art. One such embodiment would involve replacing or augmenting the line lock circuit with digital control of the correction signal. One method of doing so is described in US patent application entitled "System and Method for Achieving Wavelength Lock" filed Sep. 22, 1994.

In alternative embodiments, the duty cycle can be extended to monitor more than one absorption feature of one or more sample species contained in measurement region 34. The sample species may include the reference species, or may be other species. The absorption features may be chosen to provide specific information about the sample, such as the temperature, pressure, or reactive history of the sample. Examples include: monitoring one or more lines corresponding to molecules with high internal energies to determine the temperature of the sample as taught in the '991 patent, monitoring absorption away from the center of the absorption line to determine the pressure of the sample through the pressure dependence of the line width, and monitoring unstable states of stable molecules in reactive mixtures.

If two or more stable species are in measurement region 34, or in reference cell 52, any, or all of the species may serve as wavelength reference(s). This system can be extended to lock to two or more wavelengths $\lambda_1$, $\lambda_2$, $\lambda_n$, of these species during a measurement cycle.

Figure 3:
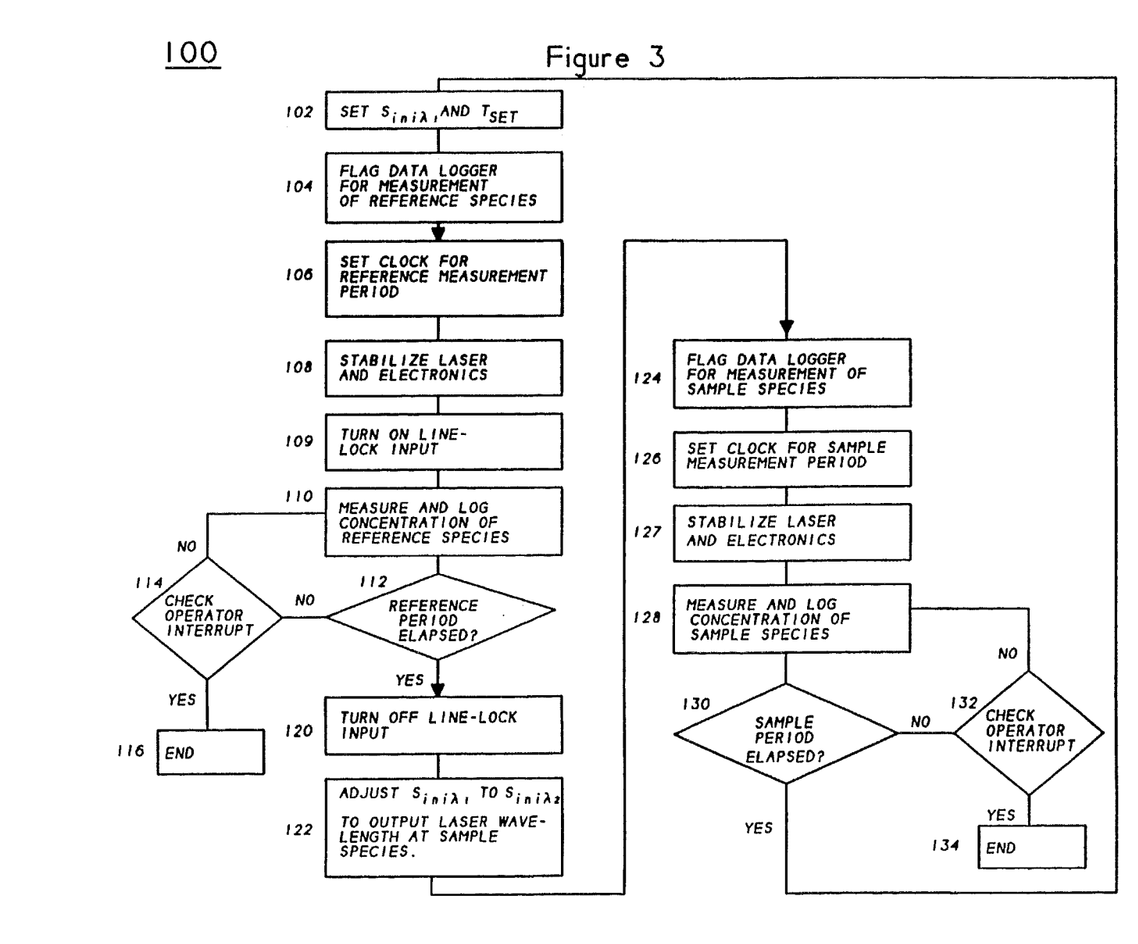
FIG. 3 is a flow chart of the software contained in the microprocessor of FIGS. 1 and 2 for implementing the off-line-locked monitor system according to this invention.

The software which accomplishes this periodic disabling of the line-lock and driving the laser diode at the adjusted drive current is shown in FIG. 3. In FIG. 3 there is a flow chart depicting the sequence of operation of alternately measuring the reference species and sample species. The microprocessor switches between measuring the reference species to measuring the sample species, and vice versa, approximately every 50 milliseconds. However, this time may vary depending upon the response time of the diode laser and detection electronics, and the rate of wavelength drift of the laser system.

Flow chart 100 of FIG. 3 begins at step 102 by driving the laser with a first DC set signal, $S_{ini\lambda_1}$, at a particular temperature to bring the laser output wavelength near $\lambda_1$, the absorption wavelength of a reference species. At step 104 the data logger of the microprocessor 50, FIG. 1, is flagged to initiate the locking and measurement sequence. In step 106 the microprocessor clock is initialized and set for the measurement period which is typically 50 milliseconds. Step 108 provides delay to allow the laser and detection electronics to stabilize after switching transients. At step 109 the line lock input is turned on and at step 110 a reference species concentration measurement can be made and logged, if required. At step 112 the system determines if the time period set for establishing the line-lock and for the reference species measurement has elapsed. If it has not, the system then proceeds to step 114 where it is determined if an operator interrupt has occurred. If it has, then the measurement is terminated at step 116; if it has not, the system loops back to step 110 where the reference species measurement is again taken and logged. If at step 112 the time period set has elapsed, the system proceeds to step 120 where the line-lock-loop is disabled. At step 122 the DC set signal is adjusted to cause the output wavelength of the laser to be at the sample species wavelength, $\lambda_2$. The data logger in microprocessor 50, FIG. 1, is then flagged to indicate that detection and measurement of the sample species is occurring at step 124 and at step 126 the clock of the microprocessor is set for the desired time period. After a delay for the laser and detection electronics stabilization, step 127, the sample species concentration is measured and logged to memory at step 128. At step 130 it is determined whether the time period has elapsed and if it has not the system proceeds to step 132 where it is determined if a user has interrupted system operation. If an interrupt has occurred the system is shut off in step 134. If no interrupt has occurred the system loops back to step 128 where another sample species concentration measurement is taken and logged to memory. If at step 130 it is determined that the time period has elapsed, the system returns to step 102 where the measurement cycle begins again. The sample concentration may be averaged over several repetitions of this cycle and output and logged to memory.

Steps 102 through 120 delineate the steps for locking on the absorption wavelength, $\lambda_1$, of a reference species and obtaining concentration measurements of the reference species. However, $\lambda_1$ can represent any number of reference species. That is, the system of this invention may sequentially lock onto and measure the concentration of a number of different reference species. Also, the same reference species may be monitored but different wavelength values of $\lambda_1$ may be locked onto to measure various features of the reference species. Moreover, a number of sample species may be sequentially monitored by adjusting the value of $S_{ini\lambda_2}$ to correspond to a number of different species.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An off-line-locked laser diode species monitor system comprising:

reference means for including at least one known species having a first absorption wavelength;

a laser source for irradiating said reference means and at least one sample species having a second absorption wavelength differing frown said first absorption wavelength by a predetermined amount;

means for locking the wavelength of said laser source to said first wavelength of said at least one known species in said reference means;

a controller for defeating said means for locking and for displacing the laser source wavelength frown said first absorption wavelength by said predetermined amount to said second absorption wavelength; and a sample detector device for determining laser radiation absorption at said second wavelength transmitted through said sample to detect the presence of said at least one sample species.

2. The off-line-locked laser diode species monitor system of claim 1 in which said reference means includes a reference cell device.

3. The off-line-locked laser diode species monitor system of claim 1 in which said reference means is a measurement region.

4. The off-line-locked laser diode species monitor system of claim 1 in which said laser source includes a diode laser.

5. The off-line-locked laser diode species monitor system of claim 4 in which said laser source includes a laser wavelength controller for adjusting the current supplied to and the temperature of said diode laser to vary the wavelength of the output.

6. The off-line-locked laser diode species monitor system of claim 1 in which said sample species is a gas which corrosively reacts with said reference cell.

7. The off-line-locked laser diode species monitor system of claim 1 in which said sample species is a transient species.

8. The off-line-locked laser diode species monitor system of claim 1 in which said sample species is in an unstable species.

9. The off-line-locked laser diode species monitor system of claim 1 in which said sample species is an excited internal state of a stable species with a low concentration under ambient conditions.

10. The off-line-locked laser diode species monitor system of claim 1 in which said sample species is contained in a measurement region.

11. The off-line-locked laser diode species monitor system of claim 10 in which said at least one known species is contained in said measurement region.

12. The off-line-locked laser diode species monitor system of claim 11 in which said sample detector device includes means for determining laser radiation absorption at said first wavelength of said at least one known species when said laser source is locked to said first wavelength for detecting the presence of said at least one known species in said measurement region.

13. The off-line-locked laser diode species monitor system of claim 12 further including means, responsive to said means for determining, for resolving the concentration of said at least one known species.

14. The off-line-locked laser diode species monitor system of claim 1 in which said means for locking includes a reference sensor device, responsive to said reference means, for producing an error signal proportional to the difference between the diode laser wavelength and the absorption wavelength of said known species.

15. The off-line-locked laser diode species monitor system of claim 12 in which said reference sensor device is a phase sensitive detector and said error signal is an odd harmonic component of the radiation transmitted through said reference species.

16. The off-line-locked laser diode species monitor system of claim 12 in which said means for locking further includes a locking circuit, responsive to said reference sensor device, for receiving said error signal and generating from said error signal a correction signal.

17. The off-line-locked laser diode species monitor system of claim 16 further including a control circuit, responsive to said locking circuit and said controller, for combining said correction signal and a first set signal from said controller to provide a first drive signal which drives said laser source at said first absorption wavelength.

18. The off-line-locked laser diode species monitor system of claim 17 in which said controller includes means for selectively defeating the error signal delivered to said locking circuit and for supplying a second set signal to said control circuit to be combined with said correction signal to provide a second drive signal to drive said diode laser from said first absorption wavelength to said second absorption wavelength of the sample species.

19. The off-line-locked laser diode species monitor system of claim 18 in which said controller further includes means for periodically actuating said control circuit to defeat the error signal delivered to the locking circuit and to supply said second set signal.

20. The off-line-locked laser diode species monitor system of claim 1 in which said controller further includes means for supplying a temperature signal to said control circuit to maintain said laser source at a desired temperature.

21. The off-line-locked laser diode species monitor system of claim 1 further including means, responsive to said means for determining, for resolving the concentration of said at least one sample species.

22. The off-line-locked laser diode species monitor system of claim 1 in which said controller includes means for driving said laser source at a plurality of said second absorption wavelengths corresponding to a plurality of sample species and said sample detector includes means for determining laser radiation absorption at said plurality of second absorption wavelengths transmitted through said sample species to detect the presence of said plurality of sample species.

23. The off-line-locked laser diode species monitor system of claim 1 in which said means for locking includes means for locking to a plurality of known species in said reference means.

24. The off-line-locked laser diode species monitor system of claim 1 in which said controller includes means for driving said laser source at a plurality of said second absorption wavelengths corresponding to a plurality of absorption features of said at least one sample species and said sample detector means includes means for determining laser radiation absorption at said plurality of second absorption wavelengths transmitted through said sample species to obtain absorption feature information.

25. An off-line-locked laser diode species monitor system comprising:

a reference cell device for including at least one known species having a first absorption wavelength;

a diode laser for irradiating said reference cell device and at least one sample species to be monitored having a second absorption wavelength differing from said first absorption wavelength by a predetermined amount;

a reference sensor device, responsive to said reference cell device, for detecting the diode laser radiation transmitted by said reference cell device;

a control circuit, responsive to said reference sensor device, for providing a first drive signal to said laser diode to lock said diode laser output wavelength to said first absorption wavelength of said species in said reference cell device;

a controller for selectively actuating said control circuit to defeat the laser diode lock and to generate a second drive signal to drive said laser diode frown said first absorption wavelength to said second absorption wavelength of the sample species to be monitored; and a sample detector device for determining the laser radiation absorption at said second wavelength transmitted through said sample to detect the presence of said at least one sample species.

26. The off-line-locked laser diode species monitor system of claim 25 in which said diode laser includes a laser wavelength controller for adjusting the diode laser input current and temperature for varying the diode laser output wavelength.

27. The off-line-locked laser diode species monitor system of claim 25 in which said sample species is a species which corrodes said reference cell.

28. The off-line-locked laser diode species monitor system of claim 25 in which said sample species is a transient species.

29. The off-line-locked laser diode species monitor system of claim 25 in which said sample species is an unstable species.

30. The of Mine-locked laser diode species monitor system of claim 25 in which said sample species is an excited internal state of a stable species with a low concentration under ambient conditions.

31. The off-line-locked laser diode species monitor system of claim 25 in which said sample species is contained in a measurement region.

32. The off-line-locked laser diode species monitor system of claim 31 in which said at least one known species is contained in said measurement region.

33. The off-line-locked laser diode species monitor system of claim 32 in which said sample detector device includes means for determining laser radiation absorption at said first wavelength of said at least one known species when said laser diode has an output wavelength equal to said first absorption wavelength to detect the presence of said at least one known species in said measurement region.

34. The off-line-locked laser diode species monitor system of claim 33 further including means, responsive to said sample detector device, for resolving the concentration of said at least one known species detected.

35. The off-line-locked laser diode species monitor system of claim 25 in which said reference sensor device produces an error signal proportional to the difference between the diode laser wavelength and the absorption wavelength of the known species.

36. The off-line-locked laser diode species monitor system of claim 35 in which said reference sensor device is a phase sensitive detector and said error signal is an odd harmonic component of the radiation transmitted through said reference species.

37. The off-line-locked laser diode species monitor system of claim 35 in which said control circuit includes a locking circuit, responsive to said reference sensor device, for receiving said error signal from said reference sensor device and for generating from said error signal a correction signal.

38. The off-line-locked laser diode species monitor system of claim 37 in which said control circuit further includes means for combining said correction signal and a first set signal received from said controller to generate said first drive signal to drive said laser diode output at said first absorption wavelength.

39. The off-line-locked laser diode species monitor system of claim 38 in which said controller further includes means for selectively defeating the error signal delivered to said locking circuit and for supplying a second set signal to said means for combining to combine said second set signal and said correction signal to generate said second drive signal to drive said laser diode output at said second absorption wavelength.

40. The off-line-locked laser diode species monitor system of claim 25 further including means, responsive to said sample detector device, for resolving the concentration of said sample species detected.

41. The off-line-locked laser diode species monitor system of claim 25 in which said controller includes means for supplying a temperature signal to said control circuit to maintain said laser source at a desired temperature.

42. The off-line-locked laser diode species monitor system of claim 25 in which said controller includes means for driving said laser source at a plurality of said second absorption wavelengths corresponding to a plurality of sample species and said sample detector includes means for determining laser radiation absorption at said plurality of second absorption wavelengths transmitted through said sample species to detect the presence of said plurality of sample species.

43. The off-line-locked laser diode species monitor system of claim 25 in which said control circuit includes means for locking to a plurality of known species in said reference cell device.

44. The off-line-locked laser diode species monitor system of claim 25 in which said controller includes means for driving said laser source at a plurality of said second absorption wavelengths corresponding to a plurality of absorption features of said at least one sample species and said sample detector means includes means for determining laser radiation absorption at said plurality of second absorption wavelengths transmitted through said sample species to obtain absorption feature information.

* * * * *